United States Patent [19]

Beerthuis et al.

[11] 4,163,108

[45] Jul. 31, 1979

[54] PROSTAGLANDINS

[75] Inventors: Roelof K. Beerthuis; David A. van Dorp, both of Vlaardingen; Diederik H. Nugteren, Rhoon, all of Netherlands

[73] Assignee: Lever Brothers Company, New York, N.Y.

[21] Appl. No.: 343,269

[22] Filed: Mar. 21, 1973

Related U.S. Application Data

[63] Continuation of Ser. No. 704,551, Feb. 12, 1968, abandoned.

[30] Foreign Application Priority Data

Feb. 16, 1967 [GB] United Kingdom ................. 7495/67

[51] Int. Cl.$^2$ .......................................... C07C 177/600
[52] U.S. Cl. .................................. 560/121; 260/413; 421/305; 421/317; 562/503
[58] Field of Search ...................... 260/468 D, 514 D; 560/121; 562/503

[56] References Cited

U.S. PATENT DOCUMENTS

| 3,598,858 | 8/1971 | Bergstrom et al. | 260/468 |
| 3,632,627 | 1/1972 | Gordon | 260/468 |
| 3,816,393 | 6/1974 | Hayashi | 260/209 |
| 3,821,279 | 6/1974 | Kuronu et al. | 260/468 |
| 3,894,062 | 7/1975 | Morozouich | 260/395 |

FOREIGN PATENT DOCUMENTS

| 2136136 | 1/1972 | Fed. Rep. of Germany | 260/468 |
| 2155546 | 5/1972 | Fed. Rep. of Germany | 260/468 |

OTHER PUBLICATIONS

Concise Chemical and Technical Dictionary, pp. 30,555 (1974).
Hackh, Chemical Dictionary, p. 23 (1969).

*Primary Examiner*—Robert Gerstl
*Attorney, Agent, or Firm*—Brumbaugh, Graves, Donohue & Raymond

[57] ABSTRACT

ω-Nor and ω-homo prostaglandins E having blood platelet aggregation-inhibiting activity are prepared by enzymatic synthesis fron nonadeca- and henicosa- -8c, 11c,14c-trienoic acids.

10 Claims, No Drawings

PROSTAGLANDINS

This is a continuation of U.S. application Ser. No. 704,551 filed Feb. 12, 1968, now abandoned.

This invention relates to prostaglandins, to processes for their preparation and to pharmaceutical preparations.

A series of related substances known as the prostaglandins, which have been found in man and other mammals, exhibit a wide range of pharmacological activities. These substances all have structures based on that of prostanoic acid (PA) which is considered to be 1α-(6'-carboxyhexyl)-5β-octylcyclopentane having the structure I, a straight chain carboxylic acid of 20 carbon atoms in the molecule internally cross-linked to form the cyclopentane ring.

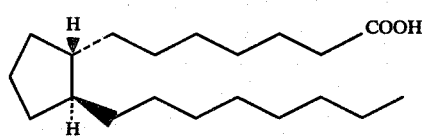

Prostaglandin $E_1$, which is commonly known as $PGE_1$, has the structure II, where the ethylenic bond is in the trans configuration and the stereochemistry at the asymmetric carbon atoms is believed to be as shown.

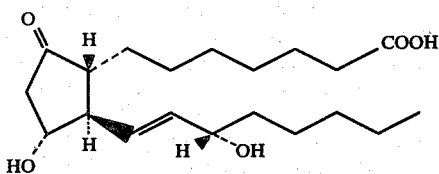

Using the Cahn-Ingold-Prelog system of notation, $PGE_1$ is 1α-(6-carboxyhexyl)-5β-(3S-hydroxy-oct-1t-enyl)-4α-hydroxycyclopentan-2-one.

The structural relationship between the prostaglandins and fatty acids suggested that the latter were precursors for prostaglandins and subsequently $PGE_1$ was made by biochemical synthesis from bishomo-γ-linolenic acid (eicosa-8c,11c,14c-trienoic acid) (the designations "c" and "t" are in this specification used to signify cis- and trans- configurations of the double bond at a position indicated), as described by van Dorp, Beerthuis, Nugteren and Vonkeman, *Biochim. Biophys. Acta,* 1964, 90, 204; *Nature,* 1964, 203, 839, and also by Bergström and his co-workers, using enzymes present in sheep vesicular glands. The acid precursors of prostaglandins are characterised by having a "skipped" double bond system in which three or more double bonds are separated by single methylene groups.

As the pharmacological activities of natural prostaglandins are diverse, including action on smooth muscle, on the cardiovascular system, on the central nervous system and in mobilisation of lipids, attempts have been made to prepare prostaglandins from fatty acids of more and of less than 20 carbon atoms in order to investigate their properties. In many instances using acids with skipped double bond systems the enzymic synthesis fails owing to enzyme specificity. Among variants tried are synthetic fatty acids having an uneven number of carbon atoms in the molecule, unlike natural fatty acids, which have even numbers of carbon atoms, and which might give rise to unnatural prostaglandins. Two such acids successfully converted into members of the prostaglandin series are nonadeca-7c,10c,13c-trienoic and heneicosa-9c,12c,15c-trienoic acids, which each have a skipped double bond system commencing at the sixth carbon atom from the terminal methyl group, as do the natural precursor acids, and differ from bishomo-γ-linolenic acid in having one less and one more methylene group on the carboxyl group side of the skipped double bond system, and are therefore referred to as α-nor and α-homo acids, giving rise to the prostaglandins α-nor-$PGE_1$ and α-homo-$PGE_1$, having the structure III, where n is 1 and m is 1 or 3, respectively.

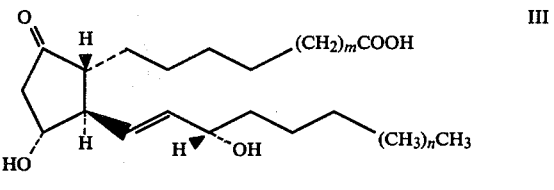

The pharmacological activities of prostaglandins have been found to be structure-specific and homologues have different properties.

It has now been discovered that nonadeca-8c,11c,14c-trienoic and heneicosa-8c,11c,14c-trienoic acids can be converted by enzymic synthesis to prostaglandins which exhibit strong pharmacological activity and separation and/or enhancement of properties by comparison with the natural prostaglandins and other synthetic prostaglandins that have been tested, including α-nor-$PGE_1$ and α-homo-$PGE_1$. These acids have a skipped double bond system and differ from bishomo-γ-linolenic acid in having one less and one more methylene group on the side of the skipped double bond system distant from the carboxylic acid group, and can therefore be referred to as ω-nor and ω-homo acids. These acids on enzymic conversion give rise to prostaglandins ω-nor-$PGE_1$ and ω-homo-$PGE_1$, having the structure III (above) where m is 2 and n is 0 or 2 respectively, their stereochemistry being that of the natural compound $PGE_1$ and believed to be as indicated. These two compounds are adjacent members of a series of prostaglandins having an uneven number of carbon atoms in the side chain containing the unsaturation and the hydroxy group.

The prostaglandins of this invention are accordingly ω-nor and ω-homo prostaglandins $E_1$, which are designated (on the basis of the accepted stereochemical structure of prostaglandin $E_1$) as 1α-(6-carboxyhexyl)-4α-hydroxycyclopentan-2-ones having in the 5β-position a 3S-hydroxy-n-alk-1t-enyl group of 7 or 9 carbon atoms. They form the class of compounds having the structure IV

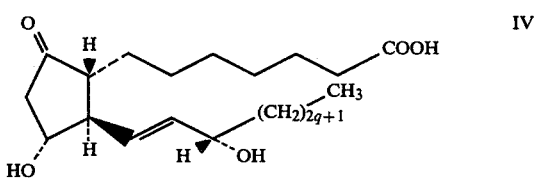

where q is an integer of from 1 to 2.

In a process of the invention a prostaglandin of the above structure IV is prepared by incubating under aerobic conditions an alka-5c,8c,11c-trienoic acid of the structure $CH_3(CH_2)_{2q}(CH_2CH=CH)_3(CH_2)_6COOH$ where q is from 1 to 2 with a prostaglandin-synthesising enzyme system prepared from animal tissue, for instance sheep vesicular gland, especially in the presence of added glutathione as co-factor. The starting acids, namely nonadeca-8c,11c,14c-trienoic and heneicosa-8c,11c,14c-trienoic, can be prepared by the selective partial hydrogenation of the corresponding triynoic acids, which are themselves obtainable by the application of classical synthetic methods, or by chain lengthening of corresponding trienoic acids of one carbon atom less using the Arndt-Eistert reaction. The conditions for the biochemical synthesis are those more fully described for prostaglandins E in U.S. patent application Ser. No. 453,483 dated May 5, 1965, now abandoned and its continuation-in-part application Ser. No. 700,030 dated Jan. 24, 1968, now abandoned and application Ser. No. 854,250 dated Aug. 29, 1969 now U.S. Pat. No. 3,579,425. The compounds can be isolated from the reaction mixture as the free acids and if required converted into acid derivative form, for instance as a carboxylic acid salt, for example the sodium, potassium or ammonium salt, or its carboxylic ester with an alcohol, for instance an alkanol of 1 to 5 carbon atoms, especially methanol or ethanol. Thus the free acids can be neutralised to give salts or converted to their methyl or ethyl esters by reaction with the appropriate amount of an ethereal solution of diazomethane or diazoethane. The free acid can be regenerated from its derivative if required.

The prostaglandins of the invention exhibit smooth-muscle contracting activity, hypotensive activity, heart stimulant activity and/or blood platelet aggregation-inhibiting activity. The following table summarises the activities found for ω-homo-PGE$_1$ and ω-nor-PGE$_1$ in comparison with a series of their close homologues obtained by analogous methods. The substances were tested as a solution of the sodium salt in a physiological saline, in comparison with PGE$_1$ as standard.

Smooth-muscle contracting activity (A) was measured by the action on the isolated guinea pig ileum using the procedure of Magnus. Blood-pressure lowering activity (B) was measured using Wistar rats at a dosage of 3 μg/kg body weight. Heart stimulant activity was measured by perfusion of an isolated rat heart using the Langendorff method modified by hanging the heart in the air and allowing the coronary perfusion rate (C1) to be measured at the same time as contractile force (C2), at dosage levels in μg/ml (Cc). Blood platelet aggregation inhibition (D) was measured in vitro using rat blood by the method of Born and O'Brien, at dosages of 0.5–1 μg/ml.

nor-PGE$_1$ showed activities of 200 and 60 respectively. ω-Homo-PGE$_1$ has also been found to inhibit ADP-induced platelet aggregation in vivo in the rat.

The ability to inhibit platelet aggregation is highly significant, as it is known that such aggregation can result in thrombosis and perhaps in atherosclerosis.

The invention accordingly includes pharmaceutical preparations comprising a prostaglandin of the invention and an inert pharmaceutically-acceptable carrier. The carrier can be a solid or a liquid in which the prostaglandin is dissolved, dispersed or suspended. The preparations are preferably in unit dosage form and can take the form of tablets, powders, capsules, solution, emulsions and liquid suspensions, especially in injectable form.

The invention and the preparation of starting materials are illustrated by the following description and Examples in which all temperatures are in °C.; TLC, RPPC and GLC are respectively thin layer chromatography, reversed phase partition chromatography and gas/liquid chromatography.

Preparation of Heneicosa-8c,11c,14c-trienoic acid (a) By Arndt-Eistert synthesis To eicosa-7c,10c,13c-trienoic acid (Struyk et al., Rec.trav.chim., 1966, 85, 1233: 127 mg, 0.41 mmol) in benzene (0.3 ml) was added oxalyl chloride (127 mg, 1 mmol), and the mixture allowed to stand at room temperature for 4 hours, after which benzene and excess oxalyl chloride were removed by a stream of nitrogen. The residual eicosa7c,10c,13c-trienoyl chloride was dissolved in benzene (0.4 ml) and the solution added dropwise to a shaken 0.4 M solution (5 ml) of diazomethane in ether at 0°. After standing for 30 minutes at 0°, excess diazomethane, benzene and ether were removed by a stream of nitrogen. The residual diazoketone was dissolved in anhydrous methanol (1 ml) and silver benzoate (44 mg) in triethylamine (0.55 ml) was added during 90 minutes, and the mixture then heated so that it boiled for 2 minutes. The resulting mixture was filtered, the residue washed with ether (1 ml) and the combined filtrates evaporated to dryness. The product was purified by TLC by the procedure of Morris, Chem. and Ind., 1962, 1238, using two plates of silica gel G (a silica gel containing 13% gypsum and made by the method of Stahl: thickness 1 mm) impregnated with 26% of silver nitrate by weight of dry silica and a mixture of benzene and ether (90:10 by volume) as eluant, giving methyl heneicosa-8c,11c,14c-trienoate as an oil (70 mg) of 99% purity as shown by GLC. This ester was saponified by treatment with 0.5 M aqueous methanolic potassium hydroxide (2 ml) at 70° for 1 hour under nitrogen, giving potassium heneicosa-8c,11c,14c,-trienoate, from which the free acid was liberated by adding dilute sulphuric acid until a mixture of pH 3 was

| Compound of Structure III | m | n | A | B | Co | C1 | C2 | D |
|---|---|---|---|---|---|---|---|---|
| ω-Homo-PGE$_1$ | 2 | 3 | 120–130 | 60–70 | 0.3 | 200 | 100–200 | 400–500 |
| ω-Nor-PGE$_1$ | 2 | 1 | 40–50 | 70–80 | 1 | 180 | 50–200 | 50–80 |
| PGE$_1$ | 2 | 2 | 100 | 70 | 1 | 200 | 50–200 | 100 |
| α-Homo-PGE$_1$ | 3 | 2 | 2 | — | 1 | 100 | 100 | 1 |
| α-Nor-PGE$_1$ | 1 | 2 | 1 | — | 1 | 100 | 100 | 0 |
| α-Nor-ω-homo-PGE$_1$ | 1 | 3 | 2 | — | 1 | 100 | 100 | 1 |
| α-Bisnor-PGE$_1$ | 0 | 2 | — | — | 1 | 120 | 100 | 2 |
| α-Bishomo-PGE$_1$ | 4 | 2 | — | — | 1 | 100 | 100 | 1 |

It will be seen that ω-nor-PGE$_1$ is a very active compound, and ω-homo-PGE$_1$ is 4 to 5 times as active as PGE$_1$ as a platelet aggregation inhibitor, and at least 3 times as active as a coronary vasodilator.

When similarly tested for blood platelet aggregation inhibition, the methyl esters of ω-homo-PGE$_1$ and ω- obtained, extracting the organic acid with light petroleum and evaporating off the solvent, leaving the free acid as an oil.

(b) Via Heneicosa-8,11,14-triynoic-acid

To a solution of non-8-ynoic acid ($n_D^{25}$ 1.4529, m.p. 20°–2°; 30.8 g, 0.2 mol) in tetrahydrofuran (100 ml) was added a 1.45 M solution (275 ml) of ethylmagnesium bromide in tetrahydrofuran during 30 minutes at 0°. The resulting mixture was stirred for 2½ hours, after which cuprous cyanide (720 mg, 4 mmol) was added and stirring was continued for 10 minutes. A solution of 1-bromododeca-2,5-diyne (Struyk et al., loc.cit., b.p. 78°–80°/0.001 mm Hg, $n_D^{25}$ 1.5055; 36.2 g, 0.15 mol) in tetrahydrofuran (75 ml) was then added during 10 minutes, and the stirred mixture heated to boiling and boiled under reflux for 15 hours: at the end of the first 4 hours another portion of cuprous cyanide (360 mg) was added. After refluxing was completed the bulk of the solvent present was distilled off under reduced pressure and to the cooled residue were added ether (100 ml) and aqueous 2N sulphuric acid. The mixture was thoroughly shaken, the ether layer which formed on standing was separated off and the aqueous layer extracted with ether; the combined ether layers were washed with saturated aqueous ammonium chloride solution, then with water, dried with anhydrous sodium sulphate and evaporated. The residue was dissolved in a small quantity of light petroleum and the solution chromatographed on a column (30 cm length and 2.2 cm diameter) of silica gel using as eluant mixtures of light petroleum and ether commencing with a proportion by volume of 95:5 and proceeding with increasing proportions of ether, with a final proportion of 40:60. The eluted fractions found to contain acid were combined and evaporated: the residue was crystallised from a mixture of light petroleum and ether (85:15 by volume) at −5° to give heneicosa-8,11,14-triynoic acid (22.7 g, 48%), m.p. 57°–8°; infrared absorption peaks at 1690 (—COOH) and 1309 cm$^{-1}$ (—CH$_2$C≡C—). The acid was converted by reaction with an ether solution of diazomethane to its methyl ester which was submitted to GLC and shown to be of 99.5% purity; mass spectrum parent peak m/e=328.

Lindlar catalyst (100 mg) and quinoline (0.05 ml) were added to a solution of heneicosa-8,11,14-triynoic acid (674 mg, 2.15 mmol) in methanol (30 ml) and the mixture shaken in hydrogen at 0° until the calculated volume of hydrogen for conversion of all acetylenic unsaturation to ethylenic unsaturation had been absorbed. The solution was filtered and poured into a mixture of water (50 ml) and 4N sulphuric acid (3 ml). The resulting mixture was extracted with 3 portions of light petroleum and the extract washed with water, dried with anhydrous sodium sulphate, and solvent removed by evaporation, leaving as residue crude heneicosa-8c,11c,14c-trienoic acid (677 mg, 98%); $n_D^{25}$ 1.4765; GLC showed the presence of 1% monoene, 9% diene and 90% triene acid. The acid (246 mg, 0.77 mmol) was converted to its methyl ester by the addition of an ethereal solution of diazomethane, and the ester purified by TLC using the method of Morris, loc.cit., using plates of silica gel G (thickness 1 mm) impregnated with 26% of silver nitrate by weight of dry silica and a mixture of benzene and ether (5:1 by volume) as eluant, giving methyl heneicosa-8c,11c,14c-trienoate as an oil (174 mg, 68%) of 99.5% purity as shown by GLC; $n_D^{25}$ 1.4695; infrared absorption peaks at 3000, 1400, 720 (cis—CH=CH—), 1743 cm$^{-1}$(—COOCH$_3$).

The ester (150 mg, 0.45 mmol) was hydrolysed by heating with 0.35N sodium hydroxide solution in 85% aqueous methanol at 60° for 1 hour under nitrogen. The reaction mixture was poured into water (100 ml), acidified to pH 3 with 4 N sulphuric acid and ether-extracted: the extracts were dried over anhydrous sodium sulphate and evaporated, to give heneicosa-8c,11c,14c-trienoic acid as an oil, $n_D^{25}$ 1.4788, estimated by its ultraviolet absorption spectrum to contain 5% of conjugated diene.

EXAMPLE 1

A mixture of heneicosa-8c, 11c,14c-trienoic acid (24 mg), glutathione (120 mg), hydroquinone (12 mg) and protein (600 mg) from the particulate enzyme fraction of the vesicular glands of sheep (obtained as described by Struyk et al., loc.cit.) suspended in aqueous 0.2 M tris(hydroxymethyl)aminomethane hydrochloride buffer solution, pH 8.0, to a total volume of 300 ml, was incubated aerobically by stirring the mixture in a large beaker open to the air at 30° for 20 minutes. The enzymic reaction was then terminated by acidification with citric acid to pH 4 and the mixture was extracted with two portions of ether (300 ml). The residue from evaporation of the extract was dissolved in chloroform and the solution chromatographed on a column of silica gel (25 g) using as successive eluants chloroform (150 ml), chloroform containing 3% methanol (150 ml), and chloroform containing 5% methanol (150 ml), and 10 ml fractions of eluate were collected. Small samples of the fractions (0.1 ml) were tested for the presence of a prostaglandin by treatment with 0.5 ml 3N potassium hydroxide in 75% aqueous methanol and examination for an ultraviolet absorption peak at 278 nm. The last fractions of the 3% methanol eluant and the first fractions of the 5% methanol eluant were found to contain the substance required: they were evaporated to give 12 mg of product. This was then purified further by RPPC using as support a diatomaceous earth (2.5 g) that had been made water-repellent by the action of a methylchlorosilane, as stationary phase a mixture (1.8 ml) of equal volumes of iso-octanol and chloroform, and as eluant aqueous methanol containing 9 volumes of methanol to 10 of water, and collecting 2 ml fractions. All those fractions shown to give the alkali reaction referred to above, except the first and the last, were combined and evaporated and the residue recrystallised from a mixture of ether and light petroleum to give 1α-(6-carboxyhexyl)-4α-hydroxy-5β-(3S-hydroxynon-1t-enyl)cyclopentan-2-one (ω-homo-PGE$_1$, 7.2 mg), m.p. 92°–3°, showing an optical rotation in methanol (1 g/liter) at 20° of −69°. Comparison with PGE$_1$ by TLC on silica gel using a mixture of chloroform, methanol, acetic acid and water in the respective proportions by volume 90:8:1:0.75, gave an $R_f$ value for ω-homo-PGE$_1$ of 0.34 as compared with 0.32 for PGE$_1$, the two substances being just separated.

EXAMPLE 2

To ω-homo-PGE$_1$ (3 mg) in ether was added an excess of an ethereal solution of diazomethane at 0°. After 5 minutes the ether was evaporated by a stream of nitrogen, leaving the ω-homo-PGE$_1$ methyl ester as an oil. The ester gave an $R_f$ value of 1.05 relative to 1.00 for PGE$_1$ methyl ester when submitted to TLC on silica gel using as eluant a mixture of chloroform and methanol in proportions of 96 to 4 by volume.

preparation of Nonadeca-8c,11c,14c-trienoic acid

To a solution of non-8-ynoic acid (3.3 g, 21 mmol) in tetrahydrofuran (10 ml) was added a 1.03 M solution (42 ml) of ethylmagnesium bromide in tetrahydrofuran during 5 minutes. The resulting mixture was stirred at 30° for 45 minutes, after which cuprous chloride (75 mg, 0.4 mmol) was added and stirring continued for 5 minutes. A solution of 1-bromodeca-2,5-diyne (Struyk et al., loc.cit.; 2.9 g, 14 mmol) in tetrahydrofuran (10 ml) was then added during 3 minutes, and the stirred mixture heated to 60° for 19 hours: at the end of the first 3 hours cuprous chloride (30 mg) was added. After heating was completed the mixture was cooled and ether (100 ml) and N hydrochloric acid were added. The mixture was thoroughly shaken, the ether layer which formed on standing was separated off and the aqueous layer extracted with ether: the combined ether layers were washed with saturated ammonium chloride solution, then with water, dried with anhydrous sodium sulphate and evaporated.

The residue (5.5 g) was dissolved in a small quantity of light petroleum and chromatographed on a silica gel column (length 30 cm, diameter 2.2 cm) using as eluant mixtures of light petroleum and ether commencing with a proportion by volume of 80:20 and proceeding with increasing proportions of ether, with a final proportion of 20:80, and fractions of eluate were collected. The eluted fractions found to contain acid were combined and evaporated: the residue was crystallised from a mixture of light petroleum and acetone (85:15 by volume) to give nonadeca-8,11,14-triynoic acid (1.9 g, 48%), m.p. 48.5°–49.5°; infrared absorption peaks at 1692 (—COOH) and 1310 cm$^{-1}$ (—CH$_2$C≡C). The acid was converted by reaction with an ether solution of diazomethane to its methyl ester, which was submitted to GLC and shown to be of 99.7% purity; mass spectrum: parent peak at m/e=300.

Lindlar catalyst (100 mg) and quinoline (0.05 ml) were added to a solution of nonadeca-8,11,14-triynoic acid (430 mg, 1.5 mmol) in methanol (30 ml) and the mixture shaken in hydrogen at 0° until the calculated volume of hydrogen for conversion of all acetylenic unsaturation to ethylenic unsaturation had been absorbed. The solution was filtered, poured into a mixture of water (50 ml) and 4N sulphuric acid (3 ml), and extracted with 3 portions of light petroleum: the extracts were washed with water, dried with anhydrous sodium sulphate, and solvent was removed by evaporation, leaving as residue crude nonadeca-8c,11c,14c-trienoic acid, n$_D^{25}$ 1.4781. The acid was converted to its methyl ester (n$_D^{25}$ 1.4694) by the addition of an ethereal solution of diazomethane, and was submitted to GLC and shown to be of 92% purity. The ester was purified further by TLC by the method of Morris, loc.cit., using plates of silica gel G (thickness 1 mm) impregnated with 26% of silver nitrate by weight of dry silica and a mixture of benzene and ether (85:15 by volume) as eluant. On evaporation of the eluate there was obtained methyl nonadeca-8c,11c,14c-trienoate as an oil (308 mg; 67%), n$_D^{25}$ 1.4696: infrared absorption peaks at 3000, 1400, 720 (broad) (cis —CH=CH—) and 1743 cm$^{-1}$ (—COOCH$_3$): GLC showed that the ester was of more than 99.5% purity; mass spectrum parent peak m/e=306; the mass spectrum showed that the position of the double bond most distant from the methoxycarbonyl group was at the 14,15-position.

The ester was saponified by treatment with 200% excess of a 0.5 M solution of potassium hydroxide in 70% aqueous methanol at 70° for 1 hour under nitrogen, giving the potassium salt, from which the free nonadeca-8c,11c,14c-trienoic acid was liberated by adding dilute sulphuric acid until a mixture of pH 3 was obtained, extracting the organic acid with light petroleum and evaporating off the solvent, leaving the free acid as an oil.

EXAMPLE 3

A mixture of nonadeca-8c,11c,14c-trienoic acid (100 mg), glutathione (500 mg), hydroquinone (30 mg) and protein (1.33 g) from the particulate enzyme fraction of the vesicular glands of sheep (obtained as described by Struyk et al., loc.cit.) suspended in aqueous 0.2 M tris(-hydroxymethyl)aminomethane hydrochloride buffer solution, pH 8.0, to a total volume of 1200 ml was incubated aerobically by stirring the mixture in a large beaker open to the air at 30° for 30 minutes. The enzymic reaction was then terminated by acidification with citric acid to pH 4 and the mixture extracted with two portions of ether (300 ml). The residue from evaporation of the extract was dissolved in chloroform and the solution chromatographed on a column of silica gel (25 g) using as successive eluants chloroform (150 ml), chloroform containing 3% methanol (150 ml), and chloroform containing 5% methanol (150 ml), and fractions of eluate were collected. The required product, as shown by test of a small sample with alkali for the formation of material showing an ultraviolet absorption peak at 278 nm, was eluted by the 5% methanol mixture and this eluate was evaporated to give crude 1α-(6-carboxyhexyl)-4α-hydroxy-5β-(3S-hydroxyhept-1t-enyl)cyclopentan-2-one (ω-nor-PGE$_1$, 6.0 mg). This was then further purified by RPPC using as support a diatomaceous earth that had been made water-repellent by the action of a methylchlorosilane, as stationary phase a mixture (1.8 ml) of equal volumes of iso-octanol and chloroform, and as eluant aqueous methanol containing 9 volumes of methanol to 10 of water. Fractions of 2 ml were collected and 0.01 ml samples were tested for the presence of prostaglandin by the alkali reaction referred to above, and all those giving the reaction except the first and the last were combined and evaporated and the residue recrystallised from a mixture of ether and light petroluem to give the pure ω-nor-PGE$_1$ (3.3 mg), m.p. 92°–3°, showing an optical rotation in methanol (1 g/liter) of −81°. Comparison with PGE$_1$ by TLC as described in Example 1 gave an R$_f$ value for ω-nor-PGE$_1$ of 0.31 as compared with 0.32 for PGE$_1$. An improved separation was obtained when the silica gel was loaded with 10% of silver nitrate, when an R$_f$ value of 0.93 was obtained relative to 1.00 for PGE$_1$.

EXAMPLE 4

ω-Nor-PGE$_1$ (3 mg) was dissolved in ether (1 ml) and an excess of an ethereal solution of diazomethane added at 0°. After 5 minutes the mixture was evaporated to dryness by a stream of nitrogen, leaving as residue ω-nor-PGE$_1$ methyl ester as an oil. The ester gave an R$_f$ value of 0.97 relative to 1.00 for PGE$_1$ methyl ester when submitted to TLC on silica gel using as eluant a mixture of chloroform and methanol in proportions of 96 to 4 by volume.

What is claimed is:

1. The prostaglandin which is a 1α-(6-carboxyhexyl)-4α-hydroxy-cyclopentan-2-one having in the 5β-position a 3S-hydroxy-n-alk-1t-enyl group of 7 or 9 carbon atoms, its pharmacologically acceptable carboxylic acid salt or its carboxylic ester with a C to $C_5$ alkanol.

2. The prostaglandin of claim 1 having a 3S-hydroxy-non-1t-enyl group.

3. The prostaglandin of claim 1 having a 3S-hydroxyhept-1t-enyl group.

4. The prostaglandin of claim 2, in the form of its free carboxylic acid or its pharmacologically acceptable carboxylic acid salt.

5. The prostaglandin of claim 3, in the form of its free carboxylic acid or its pharmacologically acceptable carboxylic acid salt.

6. The prostaglandin of claim 2, in the form of its carboxylic ester with a $C_1$ to $C_5$ alkanol.

7. The prostaglandin of claim 3, in the form of its carboxylic ester with a $C_1$ and $C_5$ alkanol.

8. The prostaglandin of claim 6, in which the ester is the methyl ester.

9. The prostaglandin of claim 7, in which the ester in the methyl ester.

10. The prostaglandin which is a 1α-(6-carboxyhexyl)-4α-hydroxy-cyclopentan-2-one having in the 5β-position a 3S-hydroxy-n-alk-1t-enyl group of 9 carbon atoms, its pharmacologically acceptable carboxylic acid salt or its carboxylic ester with an alcohol, said compounds having higher blood platelet aggregation inhibition potency compared with the corresponding $PGE_1$ compounds as measured in vitro using rat blood by the method of Born and O'Brien.

* * * * *

UNITED STATES PATENT AND TRADEMARK OFFICE
CERTIFICATE OF CORRECTION

PATENT NO. : 4,163,108
DATED : July 31, 1979
INVENTOR(S) : Roelof K. Beerthuis et al It is certified that error appears in the above-identified patent and that said Letters Patent are hereby corrected as shown below:

Col. 2, line 18, "$(CH_3)_n CH_3$" should read -- $(CH_2)_n CH_3$ --.
Col. 7, line 3, "preparation" should read -- Preparation --.
Col. 9, line 6, "Cto $C_5$" should read -- $C_1$ to $C_5$ --. Col. 10, line 4, "$C_1$ and $C_5$" should read -- $C_1$ to $C_5$ --; line 7, "the ester in" should read -- the ester is --.

Signed and Sealed this

Eleventh Day of December 1979

[SEAL]

Attest:

SIDNEY A. DIAMOND

Attesting Officer

Commissioner of Patents and Trademarks